(12) United States Patent
Kavousian et al.

(10) Patent No.: US 10,554,198 B1
(45) Date of Patent: Feb. 4, 2020

(54) LOW-POWER CLOCK CALIBRATION SYSTEM FOR MEDICAL DEVICE

(71) Applicant: Verily Life Sciences LLC, South San Francisco, CA (US)

(72) Inventors: Amirpouya Kavousian, San Jose, CA (US); Robert Wiser, San Francisco, CA (US)

(73) Assignee: VERILY LIFE SERVICES LLC, South San Francisco, CA (US)

( * ) Notice: Subject to any disclaimer, the term of this patent is extended or adjusted under 35 U.S.C. 154(b) by 0 days.

(21) Appl. No.: 15/862,511

(22) Filed: Jan. 4, 2018

Related U.S. Application Data

(60) Provisional application No. 62/442,017, filed on Jan. 4, 2017.

(51) Int. Cl.
*H03K 3/011* (2006.01)
*A61B 5/1495* (2006.01)
*A61B 5/00* (2006.01)
*A61B 5/01* (2006.01)
*A61B 5/145* (2006.01)

(52) U.S. Cl.
CPC ............... *H03K 3/011* (2013.01); *A61B 5/01* (2013.01); *A61B 5/1495* (2013.01); *A61B 5/7285* (2013.01); *A61B 5/14532* (2013.01); *A61B 2560/0252* (2013.01)

(58) Field of Classification Search
CPC .......... H03K 3/011; H03K 3/017; A61B 5/01; A61B 5/1495; A61B 5/7285; A61B 2560/0252; A61B 5/14532
See application file for complete search history.

(56) References Cited

U.S. PATENT DOCUMENTS

| | | | |
|---|---|---|---|
| 6,052,035 A | 4/2000 | Nolan et al. | |
| 6,333,939 B1 | 12/2001 | Yu et al. | |
| 2005/0007205 A1 | 1/2005 | Bridger et al. | |
| 2016/0322978 A1* | 11/2016 | Stapleton | H03L 1/02 |

* cited by examiner

*Primary Examiner* — Jung Kim
(74) *Attorney, Agent, or Firm* — Kilpatrick Townsend & Stockton LLP

(57) ABSTRACT

A clock calibration system is described herein. The clock calibration system may be implemented in a medical device to control timing of an action performed by the medical device. The clock calibration system may include a processing device coupled to a clock oscillator and a reference oscillator.

19 Claims, 5 Drawing Sheets

LOW-POWER CLOCK CALIBRATION SYSTEM FOR MEDICAL DEVICE

CROSS-REFERENCE TO RELATED APPLICATION

This application claims priority to U.S. Provisional Application No. 62/442,017, filed Jan. 4, 2017, entitled "LOW-POWER CLOCK CALIBRATION SYSTEM FOR MEDICAL DEVICE", which is hereby incorporated by reference in its entirety herein.

BACKGROUND

Hardware devices may require clocks to determine timing of certain actions. For example, a clock can be used in a medical device to deliver a drug according to a fixed interval. Such clocks can be implemented, for example, by adding real-time clock chips or low frequency crystals to hardware devices. The inclusion, however, of additional, dedicated devices for time keeping may frustrate device miniaturization goals and result in undesirable power usage.

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method for calibrating an oscillator, including: determining that a triggering event has occurred. The method also includes, in response to determining that the triggering event has occurred, activating a reference oscillator to calibrate a clock oscillator during a target interval, where the clock oscillator operates in a plurality of frequencies; determining respective pulse counts of the reference oscillator during respective individual cycles of the clock oscillator corresponding to the plurality of frequencies; and determining a number of the cycles for each of the plurality of frequencies that, when combined with the number of the cycles for each of the other frequencies of the plurality of frequencies, substantially corresponds to the target interval, where the respective numbers of the cycles are determined using the determined pulse counts corresponding to the respective frequencies. Other examples of this aspect include corresponding computer systems, apparatus, and computer programs recorded on one or more computer storage devices, each configured to perform the actions of the methods.

One general aspect includes a system, including: a processing device communicatively coupled to (i) a clock oscillator programmable to a plurality of frequencies and (ii) a reference oscillator tuned to a frequency that is higher than each frequency of the plurality of frequencies; and a memory device communicatively coupled to the processing device and including instructions for causing the processing device to perform operations including determining that a triggering event has occurred. The operations also include, in response to determining that the triggering event has occurred, activating a reference oscillator to calibrate a clock oscillator during a target interval, where the clock oscillator operates in a plurality of frequencies. The operations also include determining respective pulse counts of the reference oscillator during respective individual cycles of the clock oscillator corresponding to the plurality of frequencies. The operations also include determining a number of the cycles for each of the plurality of frequencies that, when combined with the number of the cycles for each of the other frequencies of the plurality of frequencies, substantially corresponds to the target interval, where the respective numbers of the cycles are determined using the determined pulse counts corresponding to the respective frequencies. Other examples of this aspect include corresponding methods, apparatus, and computer programs recorded on one or more computer storage devices, each configured to perform the actions described herein.

One general aspect includes one or more non-transitory computer-readable media including compute-executable instructions that, when executed by one or more computer systems, configured the one or more computer systems to perform operations including determining that a triggering event has occurred. The operations also include, in response to determining that the triggering event has occurred, activating a reference oscillator to calibrate a clock oscillator during a target interval, where the clock oscillator operates in a plurality of frequencies. The operations also include determining respective pulse counts of the reference oscillator during respective individual cycles of the clock oscillator corresponding to the plurality of frequencies. The operations also include determining a number of the cycles for each of the plurality of frequencies that, when combined with the number of the cycles for each of the other frequencies of the plurality of frequencies, substantially corresponds to the target interval, where the respective numbers of the cycles are determined using the determined pulse counts corresponding to the respective frequencies. Other examples of this aspect include corresponding computer systems, methods, and computer programs recorded on one or more computer storage devices, each configured to perform the actions described herein.

BRIEF DESCRIPTION OF THE DRAWINGS

Various examples in accordance with the present disclosure will be described with reference to the drawings, in which.

DETAILED DESCRIPTION

Examples are described herein in the context of a calibration system for a low-power time clock usable in a medical device. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Certain aspects and examples of the present disclosure relate to a clock calibration system for a medical device that is operable to control the timing of an action performed by the medical device. Non-limiting examples of medical devices employing a clock calibration system according to aspects of the present disclosure include biosensor devices, healthcare treatment devices, healthcare feedback devices, and healthcare data hubs. In one example, a continuous glucose-monitoring biosensor device includes a clock calibration system for continuous, periodic measurement of glucose of a patient. The clock calibration system calibrates a low-power oscillator serving as a time reference to the biosensor device to determine when a measurement is taken or at which the measurement reading is transmitted to a receiver device for analysis or storage. When the low-power oscillator indicates that a predetermined interval of time has passed, a control signal is output to the calibration system to actuate the biosensor device to perform the desired action. In this manner, the low-power oscillator is configured for constant operation to provide the timing for the control signal output.

Figure 1:
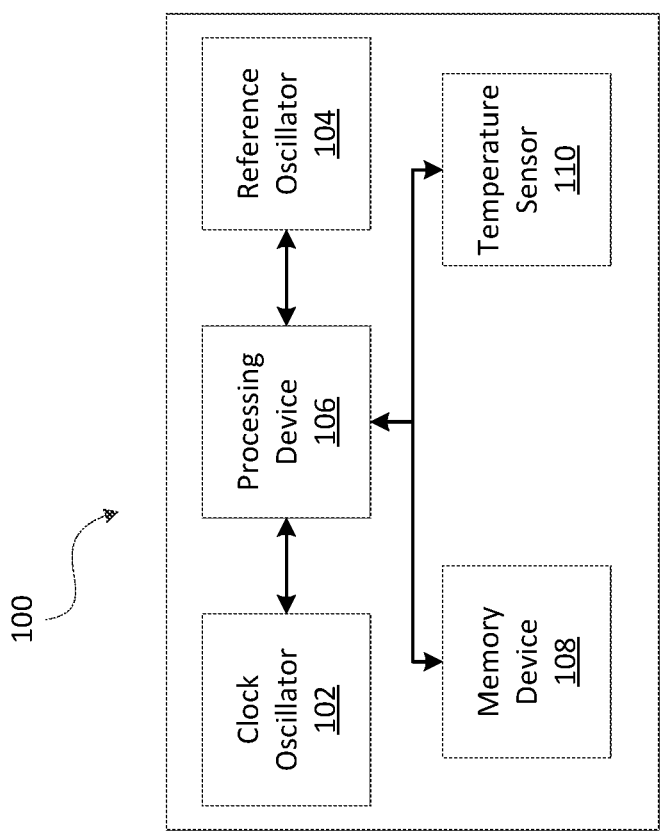
FIG. 1 illustrates an example clock system, according to at least one example.

One illustrative aspect of the present disclosure includes clock system 100 depicted in FIG. 1. The clock system 100 includes a clock oscillator 102, a reference oscillator 104, a processing device 106, and a memory device 108. The clock oscillator 102 and the reference oscillator 104 are on-chip oscillators that may be positioned on a printed circuit board ("PCB") or other component of a medical device. During operation, the clock oscillator 102 draws less current than the reference oscillator 104. For example, the clock oscillator 102 may have relatively low current consumption, drawing current between 10 and 100 Nano amps (e.g., 50 Nano amps) while the reference oscillator 104 may be a relatively high-power oscillator that draws current between 0.5 and 2 milliamps (e.g., 1 milliamp). To reduce the drain of power to the medical device, the clock oscillator 102 is used to indicate times when a control signal is outputted to operate the medical device. The reference oscillator 104 is used to periodically calibrate the clock oscillator 102 and may switch between an activated state and a deactivated state to preserve power for the biosensor device. In some aspects, the reference oscillator 104 is switched between the activated state and the deactivated state by the processing device 106.

In some aspects, the clock oscillator 102 is programmable and may be tuned to operate in multiple different frequencies. For example, the clock oscillator 102 is operable in a frequency range between one kilohertz and one megahertz. In one non-limiting example, the clock oscillator 102 is tunable between a "slow mode" frequency of approximately 50 kilohertz and a "fast mode" frequency of approximate 50.1 kilohertz (e.g., 50 kilohertz+100 hertz). The clock oscillator 102 may be sensitive to changes in temperature and changes in the supply voltage. For example, a change in temperature may slightly alter the frequency outputs in each of the programmable frequency modes of the clock oscillator 102.

In additional and alternative aspects, the reference oscillator 104 is referenced to a high-frequency crystal (e.g., a thin-film bulk acoustic resonator). The reference oscillator's 104 operating frequency is higher than the operating frequency range of the clock oscillator (e.g., above 1 megahertz). In some aspects, the reference oscillator 104 is factory-calibrated. The resulting operating frequency of the reference oscillator 104 may have minimal sensitivities to changes in temperature or power supply. Thus, the operating frequency may have minimal variation across varying supply voltages and temperatures.

The clock system 100 also includes control circuitry positioned on the PCB of the biosensor. The control circuitry includes at least a processing device 106 and a memory device 108. In some aspects, the processing device 106 is communicatively coupled to the clock oscillator 102 and the reference oscillator 104 to enable the processing device 106 to calibrate the clock oscillator 102 to the reference oscillator 104. In one example, the instructions may cause the processing device 106 to implement a counter function configured to count pulses of the reference oscillator 104 and calibrate the clock oscillator 102 using the number of pulses counted during respective cycles of the clock oscillator 102 at different frequencies. The processing device 106 may execute computer-executable program instructions stored on the memory device 108 for calibrating the clock oscillator 102. The clock oscillator 102 can output one or more timing signals to cause the processing device 106 to output one or more control signals to one or more other circuitries in the medical device (e.g., a biosensor device) to cause the medical device to perform a desired action (e.g., retrieve a measurement, transmit a measurement, etc.). Non-limiting examples of the processing device 106 include a microprocessor, a digital signal processor ("DSP"), an application-specific integrated circuit ("ASIC"), field programmable gate arrays ("FPGAs"), or other processing means for processing electrical signals received via the biosensor circuitry. The memory device 108 may also include a cache, data store, or other storage means for storing values and information determined or received by the processing device 106.

The clock oscillator's 102 programmability (e.g., capability to operate in multiple frequencies) and the use of each of the multiple frequencies during calibration is beneficial to improving the accuracy of the clock system 100. For example, using the multiple frequencies improves the time resolution of the clock oscillator 102. In a conventional clock system in which an oscillator is configured using only a single frequency, the time period is limited to a single cycle of the oscillator. In contrast, the time resolution for the clock system 100 is improved to provide a more accurate time measurement. For example, the clock oscillator 102 may be operable in two frequencies, one slow frequency and one fast frequency. The time resolution is a difference between respective cycles of the two frequencies. As cycles of the fast clock are subtracted and cycles of the slow clock are added to calibrate the clock oscillator 102 to the reference oscillator 104, the total operational time of the clock oscillator 102 to perform both cycles changes by the difference of the two frequencies. In additional examples, the clock oscillator 102 is operable in three or more frequencies. Using more frequencies of the clock oscillator 102 during calibration will further improve the time resolution to provide increased accuracy of the time measurement.

The clock system 100 can include a temperature sensor 110. The temperature sensor 110 is communicatively coupled to the processing device 106. In some aspects, the temperature sensor 110 is programmed to turn off, and then periodically back on at predetermined intervals to sense the temperature surrounding the clock system 100. For example, the memory device 108 may include instructions for causing the processing device 106 to activate the temperature sensor 110 every 10 minutes to sense the temperature. In some aspects, the intervals for activating the temperature sensor 110 may be determined by the clock oscillator 102. In other aspects, the temperature sensor 110 includes, or is communicatively coupled to, an active timer. The active timer may cause the processing device 106 to activate the temperature sensor 110 more frequently than the predetermined intervals in response to a change in temperature measured by the temperature sensor 110. For example, since temperature changes may be several times the temperature resolution of the temperature sensor 110, the temperature sensor 110 may not accurately capture rapid changes in the temperature. To capture rapid temperature changes, the adaptive timer may reduce the time interval between subsequent measurements when the temperature sensor 110 first indicates a change.

The temperature sensor 110 may transmit signals indicative of the temperature in or proximate to the clock system 100 to the processing device 106. The processing device 106 may compare the temperature received from the temperature sensor 110 to previous temperature readings stored in the memory device 108 to determine whether a change in the temperature has occurred. The processing device 106 can store the temperature received from the temperature sensor 110 in the memory device 108. A determination that a change in the temperature has occurred above a predetermined threshold causes the processing device 106 to activate the reference oscillator 104 and initiate a calibration process for the clock oscillator 102 using the reference oscillator 104. For example, a variation threshold value of 0.5 degrees Celsius may be stored (e.g., as a factory pre-configuration, operator configured, or system-determined in real-time) in the memory device 108. The processing device 106 may determine that the temperature has changed one (1) degrees Celsius in response to receiving a temperature reading from the temperature sensor 110. Because the one-degree change is greater than the variation threshold of 0.5, the processing device 106 can activate the reference oscillator 104. Although the temperature sensor 110 is shown as integral to the clock system 100, the temperature sensor 110 may be separate from the clock system 100 without departing from the scope of the present disclosure. Similarly, one or more of the components may be added or removed from the clock system 100 of FIG. 1, or a function described herein may be present in separate components without departing from the scope of the present disclosure.

Figure 2:
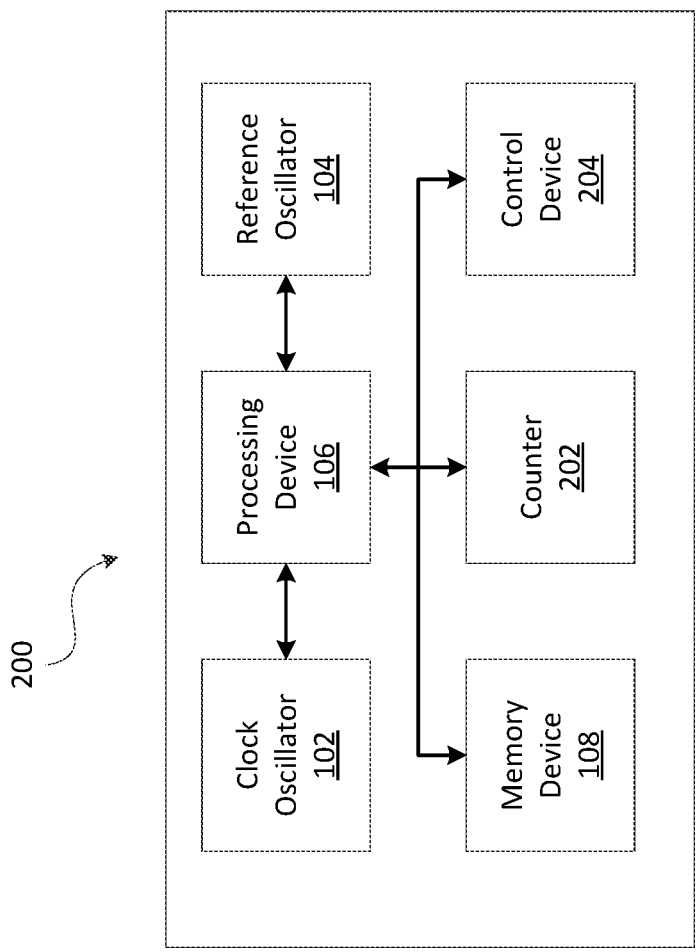
FIG. 2 illustrates an example clock system, according to at least one example.

For example, FIG. 2 depicts an example of a clock system 200 that includes the clock oscillator 102, the reference oscillator 104, the processing device 106, and the memory device 108 of the clock system 100 of FIG. 1. The clock system 200 also includes a counter 202 and a control device 204. The counter 202 and the control device 204 are separate from the processing device 106 and are configured to perform the functions corresponding to certain instructions stored the memory device 108 and executed by the processing device 106 as described in FIG. 1. For example, the counter 202 may include a separate oscillator, digital timer, or other counting means to count pulses corresponding to one or both of the clock oscillator 102 or the reference oscillator 104. The control device 204 may include circuitry to generate the control signals for operating the biosensor device to take or transmit a measurement. For example, the clock oscillator 102 may indicate that the target interval has elapsed and that it is the proper time to transmit a control signal for controlling the biosensor. The processing device 106 may transmit a signal to the control device 204 instructing the control device 204 to transmit the control signal. In some aspects, the control device 204 includes a processing device 106 or other processing means separate from the processing device 106.

Figure 3:
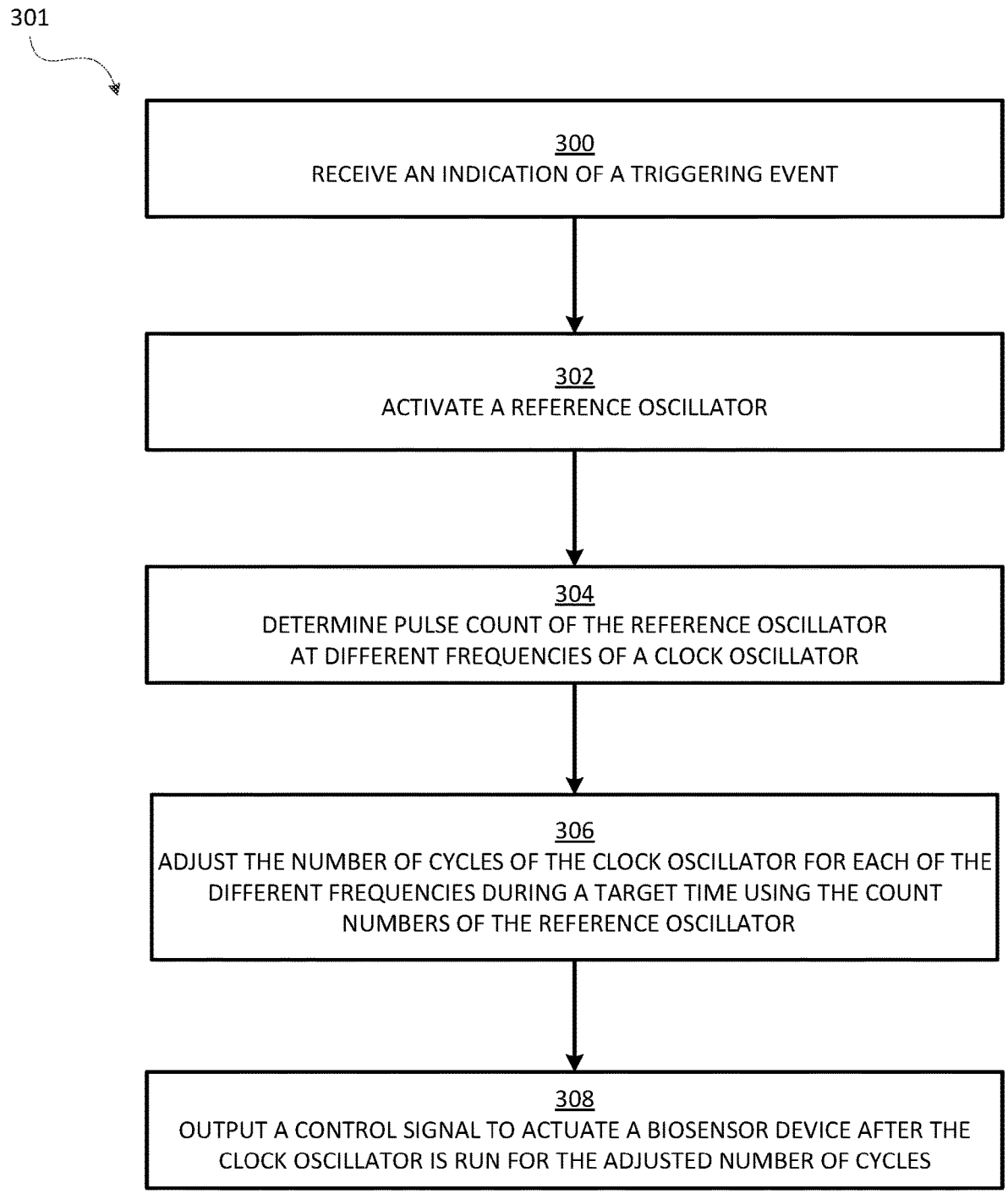
FIG. 3 illustrates a flow chart showing an example process for calibrating aspects of a clock system, according to at least one example.

FIG. 3 is a flow chart of an example process 301 for calibrating the clock oscillator 102 using the reference oscillator 104. The process is described with respect the systems 100, 200 of FIGS. 1 and 2, though other implementations are possible without departing from the scope of the present disclosure.

In block 300, an indication of a triggering event is received. In some aspects, the indication is received by the processing device 106. In one example, the processing device 106 receives the indication in the form of an electrical signal generated and transmitted by the temperature sensor 110. The electrical signal may correspond to a temperature measurement of the environment surrounding the biosensor or the clock oscillator 102. The temperature measurement indicates a triggering event when a difference between the temperature measurement and a stored measurement corresponding to a temperature measurement previously transmitted by the temperature sensor 110 is beyond a predetermined threshold. For example, the temperature sensor 110 may have previously transmitted an electrical signal to the processing device 106 indicating that the temperature was 25 degrees Celsius. In the next sensing cycle, the temperature sensor 110 may indicate that the temperature is 24 degrees Celsius. A threshold temperature value of 0.5 degrees Celsius may be stored in a cache of the memory device 108. The processing device 106 may retrieve the previous temperature measurement and determine the change in temperature based on the difference between the previous temperature measurement and the temperature measurement newly received from the temperature sensor 110 (e.g., one degree Celsius) and determine that it is above the temperature threshold and that a triggering event exists.

In another aspect, the triggering event corresponds to an interval of time that has elapsed since the clock oscillator was calibrated. For example, the processing device 106 may be configured to calibrate the clock oscillator 102 every ten minutes, so the triggering event is an indication that ten minutes has elapsed. In some aspects, the indication is an electrical signal or other indicator (e.g., pulse count, observation, etc.) that ten minutes has elapsed may come from one or more of the counter 202 (e.g., counting cycles of the clock oscillator until the counter 202 reaches a value that indicates a ten-minute time lapse) or the processing device 106 or control device 204 observing that the ten-minute time has passed.

In a further aspect, the triggering event corresponds to a transmission of data by a transmitter of the biosensor device. In some aspects, the typical packet length may be multiple cycles of the clock oscillator 102. Performing a calibration during a transmission may reduce the time needed to activate the reference oscillator 104 for calibration.

In block 302, the reference oscillator 104 is activated in response to determining that the triggering event of block 300 has occurred. In some aspects, the reference oscillator 104 is configured to remain in an inactive, or "off," state until a calibration process is triggered in response to a triggering event as described in block 300. The reference oscillator 104 may be activated by one of the processing device 106 or the control device 204.

In block 304, pulse counts of the reference oscillator 104 are determined at different frequencies of a clock oscillator 102. In some aspects, the clock oscillator 102 is run concurrently with the reference oscillator 104 and the pulses, or cycles, of the reference oscillator 104 are compared with the clock oscillator 102 running in each programmed frequency mode (e.g., the fast mode and the slow mode).

Figure 4:
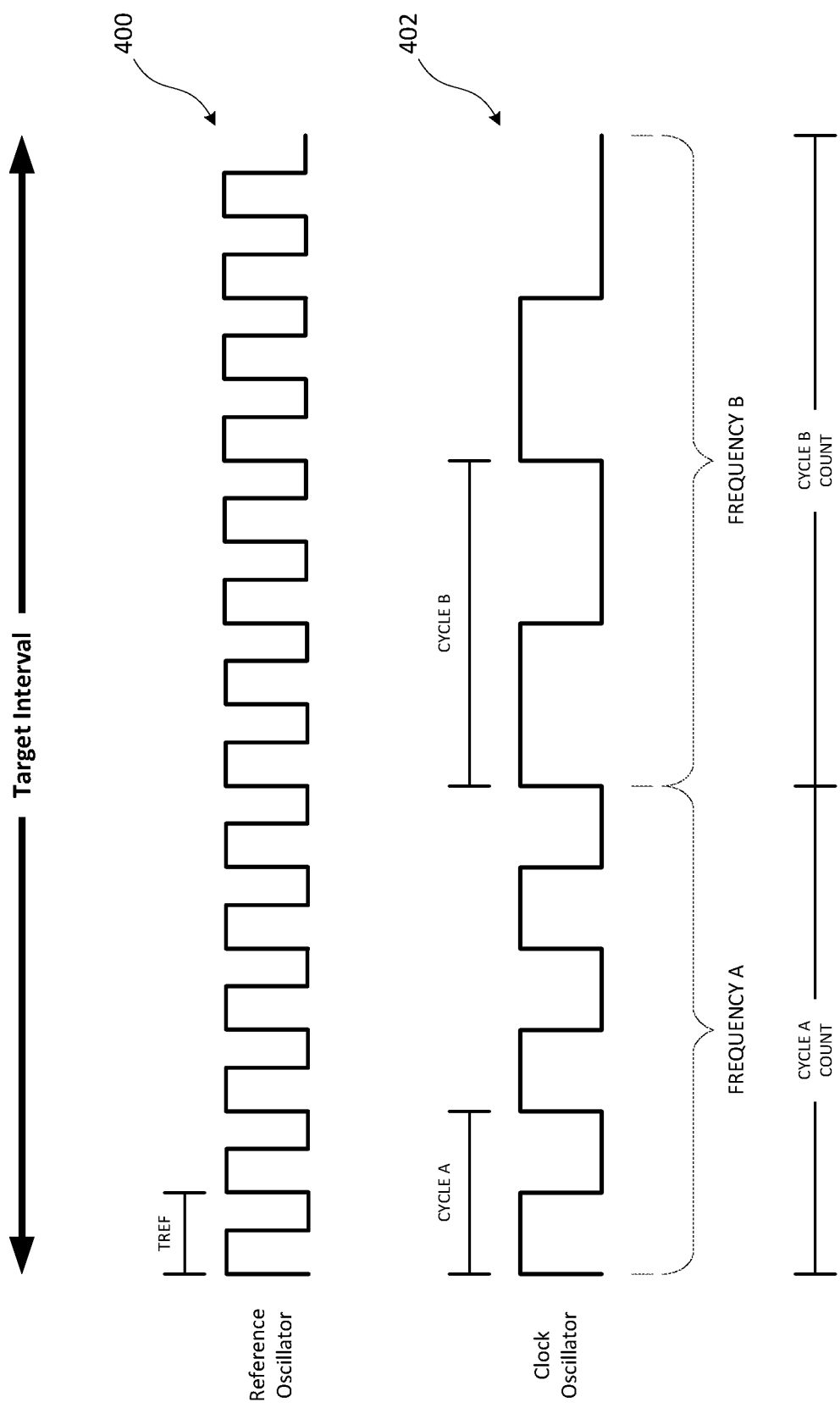
FIG. 4 illustrates a graphical depiction of an example comparison of data from a reference oscillator with data of a clock oscillator, according to at least one example.

FIG. 4 is an example of comparison of pulses 400 of the reference oscillator 104 to cycles 402 of the clock oscillator 102. The operation of the clock oscillator 102 and the reference oscillator 104 is shown over a target interval. The target interval may correspond to the interval of time between the biosensor device performing an action in response to a control signal. In some examples, the target interval may correspond to an interval of time that begins before or after the control signal is sent and ends before or after the biosensor device performs the action. In one example, the target interval corresponds to one second (1 s) and after each second, the clock system 100, 200 outputs a control signal to control the biosensor device's performance of the action.

Each of the pulses 400 of the reference oscillator 104 is designated TREF in FIG. 4. TREF corresponds to a reference time that it takes for the reference oscillator 104 to complete one oscillation (e.g., pulse, cycle). Each of the cycles 402 of the clock oscillator 102 is designated CYCLE A or CYCLE B depending on the frequency mode in which the clock oscillator 102 is operating. In the example shown in FIG. 4, the clock oscillator is tuned to a first mode having FREQUENCY A. During the first mode, each oscillation, or cycle, of the clock oscillator 102 is designated CYCLE A. The clock oscillator 102 then switches to a second mode having FREQUENCY B at which each cycle is designated CYCLE B. In comparing the pulses 400 to the cycles 402 of FIG. 4, the number of pulses 400 (e.g., TREF) are determined for one cycle (e.g., CYCLE A) at the first frequency, FREQUENCY A, and the number of pulses 400 are determined for one cycle (e.g., CYCLE B) at the second frequency, FREQUENCY B. In FIG. 4, N1 corresponding to the number of pulses 400 in CYCLE A is two (2) and N2 corresponding to the number of pulses in CYCLE B is four (4). Although only two frequency modes are described for the clock oscillator 102, the clock oscillator 102 may be programmed for additional frequencies modes (e.g., three or more) without departing from the scope of the present disclosure. In some aspects, the use of additional frequency modes in the calibration process may improve the time resolution.

The reference oscillator 104 maintains substantially the same number of pulses 400 over the target interval despite changes in conditions, such as temperature or supply voltage. The clock oscillator cycles 402 may change significantly or slightly depending on changes in temperature or supply voltage. As such, the comparison of the cycles 402 to the pulses 400 is indicative of whether a condition has changed that is affecting the operation of the clock oscillator 102 at one or each different frequency modes. In some aspects, the counts of the pulses 400 in each cycle 402 may be stored in a cache or other storage means of the memory device 108 for comparison with previous pulse counts. To the extent, the pulse counts for each frequency mode of the clock oscillator 102 match the pulse counts stored immediately prior, no calibration may be necessary.

Returning to FIG. 3, in block 306, the number of cycles of the clock oscillator 102 for each of the different frequency modes (or their respective frequencies) within the target time is adjusted using the count numbers of the reference oscillator 104. The number of cycles corresponds to the number of CYCLE As and the number of CYCLE Bs at FREQUENCY A and FREQUENCY B, respectively, that are necessary to generate a continuous set of cycles 402 for the duration of the target interval. In some aspects, where the pulse counts for each frequency mode of the clock oscillator 102 matches pulse counts stored in the memory device 108 (but not those stored immediately prior), the number of cycles of the clock oscillator 102 for each frequency mode may be adjusted corresponding to cycle counts stored and associated with the pulse counts in the memory device 108. In additional and alternative aspects, the number of cycles of the clock oscillator 102 for each frequency mode may be determined by the processing device 106.

In one example, the processing device 106 determines the number of cycles of the clock oscillator 102 for each frequency mode by estimating the number of cycles of the clock oscillator 102 needed to complete the target interval in one of the two frequency modes. The processing device 106 then performs a linear search from this estimate to determine a target combination of cycles in each of the frequency modes that yields a duration approximately matching the target interval with an error below an error threshold. In some aspects, the initial estimate of the number of clock oscillator 102 cycles needed to complete the target interval is based on calibration information, measured data, or other information stored in the memory device 108. In additional and alternative aspects, a linear search for a target combination of a cycle in two different frequency modes includes incrementally reducing the estimate for the number of cycles of the first cycle by an amount (e.g., one) and increasing, from zero, the number of cycles of the second cycle by the same amount. For example, the memory device 108 may include the following instructions executable by the processing device 106 to perform the linear search:

$$N1s = X1*N1 + X2*N2 \quad \text{(Equation 1)}$$

$$N1s < \tfrac{1}{2} LSB(N2-N1) \quad \text{(Equation 2)}$$

wherein N1 and N2 are the pulse counts determined for a cycle in the first mode and second mode, respectively, as described in block 302, X1 and X2 are the varying estimates of the number of cycles for the first mode and the second mode, respectively. Equation 2 corresponds to the error threshold. X1 and X2 may be varied until N1s is less than half the difference of the pulse counts (e.g., N2−N1).

In block 308, a control signal is output after the clock oscillator 102 is run at the adjusted number of cycles determined in block 306 to control the biosensor. For example, after the clock oscillator 102 is run in the first mode for the first number of cycles (X1) determined in block 306, the clock oscillator 102 switches to the second mode and runs in the second mode for the second number of cycles (X2) determined in block 306. Following each iteration of the clock oscillator 102 running in each of the two modes at the determined number of cycles, the processing device 106 of FIG. 1 or the control device 204 of FIG. 2 transmits a control signal to the biosensor circuitry of the biosensor device to cause the biosensor device to perform a desired action (e.g., measurement, transmission).

Figure 5:
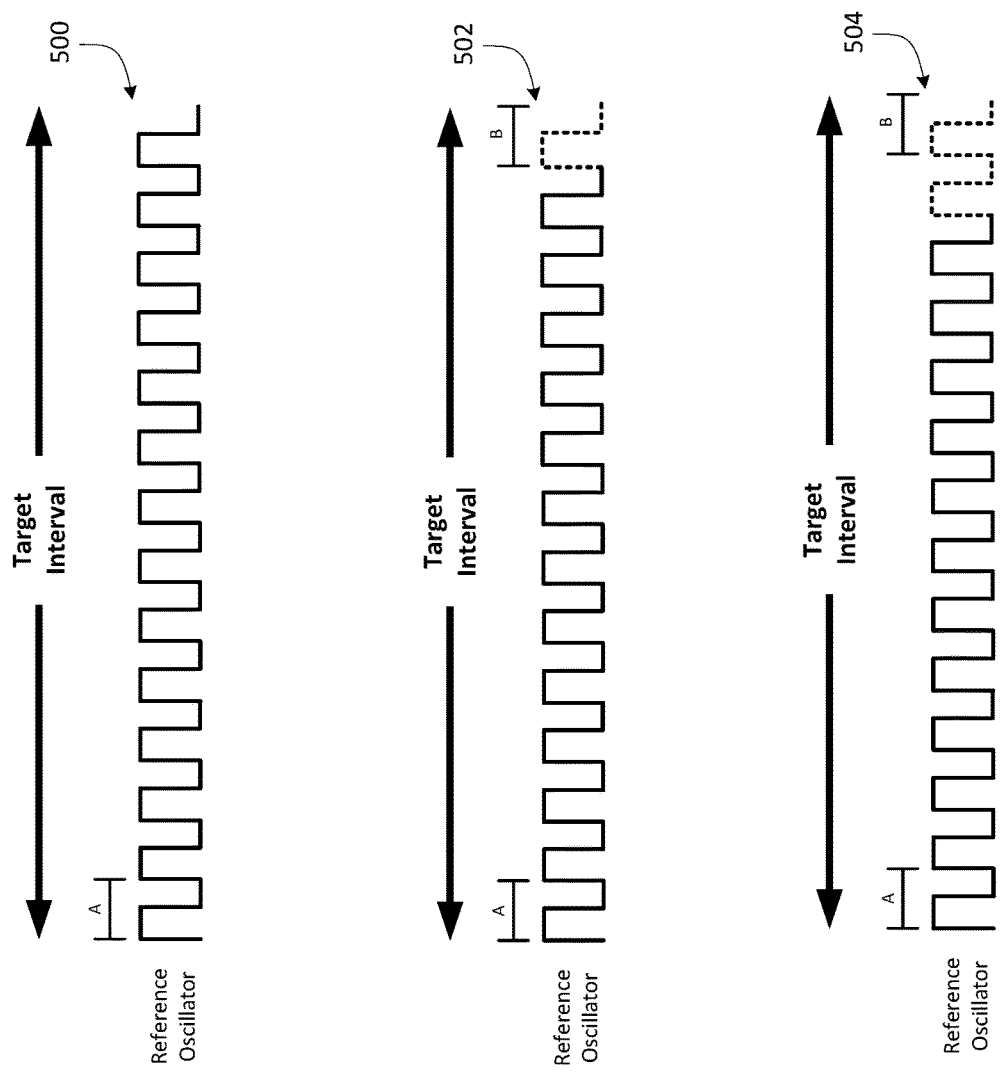
FIG. 5 illustrates a graphical depiction of an example a linear search for a combination of cycles, according to at least one example.

FIG. 5 is an example of three iterations of a linear search for a combination of cycles of two frequency modes to yield a target interval according to aspects of the present disclosure. The cycles are not drawn to scale as they are intended only as visual illustration of the linear search described in block 306 of FIG. 3. In the first iteration, the cycles 500 correspond to an estimate of the number of cycles in the first frequency mode ("A") are needed to match the target interval. In the second iteration, the cycles 502 correspond to a reduction of the number of cycles in the first frequency mode by one and an increase, from zero, of the number of cycles in the second frequency mode ("B") by one. In the third iteration, the cycles 504 correspond to a second reduction of the number of cycles in the first frequency mode by another one and an increase of the number of cycles in the second frequency mode by another one. The linear search may continue until the error is below the error threshold as determined by Equations 1 and 2.

The error may correspond to any one source or combination of sources. Non-limiting examples of error sources may include slight frequency instability of the reference oscillator 104, temperature variations, the time resolution, time errors during mode-switching of the clock oscillator 102, and resolution of the temperature sensor. Equations 1 and 2 may ensure that the error is minimized (e.g., below the error threshold) to yield a more accurate timing In some aspects, the calibration results of the process described in FIG. 3 may be stored in the memory device 108. In further aspects, the calibration results may be referenced in future calibrations and used to recalibrate the clock oscillator 102 without performing the process of FIG. 3. For example, the calibration results may be stored in a table and associated with the temperature measurement of the temperature sensor 110 or other indicator of the triggering event for reference. In response to an indication of a triggering event such as a temperature measurement received from the temperature sensor 110, the temperature measurement may be referenced in the table and, if present, the calibration data associated with the temperature measurement may be used to recalibrate the clock oscillator 102. In additional aspects, a timestamp may be stored in the table and associated with the temperature measurement. The timestamp may indicate the period since the last calibration using the associated temperature measurement. A time threshold may be separately stored in the memory device 108. The time threshold may indicate whether a temperature measurement associated with the timestamp is expired (e.g., stale). For example, a timestamp beyond the time threshold indicates that the timestamp is expired and a timestamp within the time threshold indicates that the timestamp is not expired. Subsequent to determining that a stored temperature matches the temperature measurement of the temperature sensor 110, the timestamp may be compared to the temperature threshold and the stored temperature measurement associated with the timestamp is used to calibrate the clock oscillator 102 only if the timestamp is not expired.

In some aspects, the temperature measurement is not present in the stored table, the reference oscillator 104 may be turned on to perform the calibration as described in FIG. 3. In additional and alternative aspects, if the temperature measurement is between two stored temperature measurements, the calibration data for the two stored temperature measurements may be interpolated for points between the two stored temperatures and used to recalibrate the clock oscillator 102.

The following table is an example of a table that may be stored in the memory device 108 to include calibration information:

| Temperature (Triggering Event) | Clock Oscillator Tuning Code | Timestamp of Calibration |
| --- | --- | --- |
| 0 | 27 | 0 (factory calibration) |
| 20 | 24 | 101 |
| 40 | 21 | 55 |
| 60 | 18 | 74 |
| 80 | 15 | 96 |

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

The invention claimed is:

1. A method for calibrating an oscillator, comprising:
determining that a triggering event has occurred;
in response to determining that the triggering event has occurred, activating a reference oscillator to calibrate a clock oscillator during a target interval, wherein the clock oscillator operates in a plurality of frequencies;
determining respective pulse counts of the reference oscillator during respective individual cycles of the clock oscillator corresponding to the plurality of frequencies;
determining a number of the cycles for each of the plurality of frequencies that, when combined with the number of the cycles for each of the other frequencies of the plurality of frequencies, substantially corresponds to the target interval, wherein the respective numbers of the cycles are determined using the determined pulse counts corresponding to the respective frequencies;
storing the determined number of the respective cycles for each of at least two different frequencies by associating the determined number of the respective cycles for each of the at least two different frequencies with the triggering event;
receiving an indication of a temperature measurement from a temperature sensor, the temperature measurement corresponding to the triggering event; and
prior to activating the reference oscillator subsequent to receiving the indication of the temperature measurement, comparing the temperature measurement with stored temperature measurements to determine whether the clock oscillator was previously calibrated in response to the same temperature measurement.

2. The method of claim 1, wherein the method further comprises outputting, via the clock oscillator, a control signal to time an action of a medical device subsequent to the clock oscillator operating at the corresponding numbers of the cycles at respective frequencies of the clock oscillator.

3. The method of claim 1, wherein determining, for each frequency of the plurality of frequencies, the respective numbers of the cycles comprises:
 estimating a cycle count corresponding to the number of cycles for a first frequency of the plurality of frequencies matching the target interval; and
 performing a linear search using the estimated cycle count to determine the respective numbers of the cycles for each frequency of the plurality of frequencies.

4. The method of claim 3, wherein performing the linear search comprises:
 incrementally decreasing the number of cycles for the first frequency;
 incrementally increasing the number of cycles for a second frequency of the plurality of frequencies; and
 repeating said incrementally decreasing and said incrementally increasing until an error value corresponding to the respective numbers of cycles for the first frequency and the second frequency is below an error threshold determined by half of a difference between the pulse counts of the reference oscillator during the cycles of the clock oscillator for each frequency of the plurality of frequencies.

5. The method of claim 1, wherein the triggering event corresponds to a temperature change above a predetermined temperature threshold,
 wherein the method further comprises storing a first temperature measurement in a manner that associates the first temperature measurement with the respective pulse counts, the first temperature measurement corresponding to a temperature at a time of the triggering event.

6. The method of claim 1, further comprising recalibrating the clock oscillator using a corresponding measurement of the stored temperature measurement in response to determining that the clock oscillator was previously calibrated in response to the same triggering event, the corresponding measurement matching the temperature measurement.

7. The method of claim 1, further comprising:
 comparing a timestamp associated with a corresponding measurement of the stored temperature measurements with a time threshold, the corresponding measurement matching the temperature measurement;
 determining that the timestamp is within the time threshold; and
 recalibrating the clock oscillator using the corresponding measurement in response to said determining that the timestamp is within the time threshold.

8. The method of claim 1, further comprising:
 comparing a timestamp associated with a corresponding measurement of the stored temperature measurements with a time threshold, the corresponding measurement matching the temperature measurement;
 determining that the timestamp is beyond the time threshold; and
 recalibrating the clock oscillator using the reference oscillator in response to said determining that the timestamp is beyond the time threshold.

9. The method of claim 1, wherein activating the reference oscillator comprises activating the reference oscillator to calibrate the clock oscillator to operate in each frequency of the plurality of frequencies during the target interval.

10. A system, comprising:
 a processing device communicatively coupled to (i) a clock oscillator programmable to a plurality of frequencies and (ii) a reference oscillator tuned to a frequency that is higher than each frequency of the plurality of frequencies; and
 a memory device communicatively coupled to the processing device and including instructions for causing the processing device to perform the following operations:
 determining that a triggering event has occurred;
 in response to determining that the triggering event has occurred, activating the reference oscillator to calibrate the clock oscillator during a target interval;
 determining respective pulse counts of the reference oscillator during respective individual cycles of the clock oscillator corresponding to the plurality of frequencies; and
 determining a number of the cycles for each of the plurality of frequencies that, when combined with the number of the cycles for each of the other frequencies of the plurality of frequencies, substantially corresponds to the target interval, wherein the respective numbers of the cycles are determined using the determined pulse counts corresponding to the respective frequencies;
 storing the determined number of the respective cycles for each of at least two different frequencies by associating the determined number of the respective cycles for each of the at least two different frequencies with the triggering event;
 receiving an indication of a temperature measurement from a temperature sensor, the temperature measurement corresponding to the triggering event; and
 prior to activating the reference oscillator subsequent to receiving the indication of the temperature measurement, comparing the temperature measurement with stored temperature measurements to determine whether the clock oscillator was previously calibrated in response to the same temperature measurement.

11. The system of claim 10, wherein the system is implemented in a device comprising a biosensor.

12. The system of claim 10, wherein:
 the processing device is further communicatively coupled to a counter; and
 determining the respective pulse counts comprises determining by the counter.

13. The system of claim 10, wherein the operations further comprise outputting, via the clock oscillator, a control signal to time an action of a medical device subsequent to the clock oscillator operating at the corresponding numbers of the cycles at respective frequencies of the clock oscillator.

14. The system of claim 13, wherein the action of the medical device comprises retrieving a medical measurement or transmitting a medical measurement.

15. One or more non-transitory computer-readable media comprising compute-executable instructions that, when executed by one or more computer systems, configures the one or more computer systems to perform operations comprising:
 determining that a triggering event has occurred;
 in response to determining that the triggering event has occurred, activating a reference oscillator to calibrate a clock oscillator during a target interval, wherein the clock oscillator operates in a plurality of frequencies;

determining respective pulse counts of the reference oscillator during respective individual cycles of the clock oscillator corresponding to the plurality of frequencies; and determining a number of the cycles for each of the plurality of frequencies that, when combined with the number of the cycles for each of the other frequencies of the plurality of frequencies, substantially corresponds to the target interval, by at least:

estimating a cycle count corresponding to the number of the cycles for a first frequency of the plurality of frequencies matching the target interval; and performing a linear search using the estimated cycle count to determine the respective numbers of the cycles for each frequency of the plurality of frequencies by at least:

incrementally decreasing the number of the cycles for the first frequency;

incrementally increasing the number of the cycles for a second frequency of the plurality of frequencies; and repeating said incrementally decreasing and said incrementally increasing until an error value corresponding to the respective numbers of the cycles for the first frequency and the second frequency is below an error threshold determined by half of a difference between the pulse counts of the reference oscillator during the cycles of the clock oscillator for each frequency of the plurality of frequencies, wherein the respective numbers of the cycles are determined using the determined pulse counts corresponding to the respective frequencies.

16. The one or more non-transitory computer-readable media of claim 15, wherein the operations further comprise outputting, via the clock oscillator, a control signal to time an action of a medical device subsequent to the clock oscillator operating at the corresponding numbers of the cycles at respective frequencies of the clock oscillator.

17. The one or more non-transitory computer-readable media of claim 15, wherein the triggering event corresponds to a temperature change above a predetermined temperature threshold, wherein the operations further comprise storing a temperature measurement in a manner that associates the temperature measurement with the respective pulse counts, the temperature measurement corresponding to a temperature at a time of the triggering event.

18. The one or more non-transitory computer-readable media of claim 15, wherein the operations further comprise:

storing the determined number of the respective cycles for each of at least two different frequencies by associating the determined number of the respective cycles for each of the at least two different frequencies with the triggering event.

19. The one or more non-transitory computer-readable media of claim 18, wherein the operations further comprise:

receiving an indication of a temperature measurement from a temperature sensor, the temperature measurement corresponding to the triggering event; and prior to activating the reference oscillator subsequent to receiving the indication of the temperature measurement, comparing the temperature measurement with stored temperature measurements to determine whether the clock oscillator was previously calibrated in response to the same temperature measurement.

\* \* \* \* \*